US012636419B2

(12) United States Patent
Biller

(10) Patent No.: US 12,636,419 B2
(45) Date of Patent: May 26, 2026

(54) METHOD OF CONVERTING A FEMORAL VENOUS CANNULA

(71) Applicant: enableCV, LLC, Midvale, UT (US)

(72) Inventor: William T. Biller, Tustin, CA (US)

(73) Assignee: enableCV, LLC, Midvale, UT (US)

( * ) Notice: Subject to any disclaimer, the term of this patent is extended or adjusted under 35 U.S.C. 154(b) by 115 days.

(21) Appl. No.: 18/063,000

(22) Filed: Dec. 7, 2022

(65) Prior Publication Data

US 2023/0107515 A1    Apr. 6, 2023

Related U.S. Application Data

(63) Continuation of application No. 16/513,575, filed on Jul. 16, 2019, now abandoned, which is a continuation of application No. PCT/US2017/013645, filed on Jan. 16, 2017.

(51) Int. Cl.
*A61M 1/36* (2006.01)
*A61M 25/00* (2006.01)

(52) U.S. Cl.
CPC ........ *A61M 1/3659* (2014.02); *A61M 1/3666* (2013.01); *A61M 25/0045* (2013.01); *A61M 25/007* (2013.01); *A61M 25/0074* (2013.01); *A61M 2205/04* (2013.01); *A61M 2210/125* (2013.01)

(58) Field of Classification Search
CPC .............. A61M 1/3659; A61M 1/3666; A61M 25/0045; A61M 25/007; A61M 25/0074; A61M 2205/04; A61M 2210/125; A61M 2025/0079; A61M 2210/127
See application file for complete search history.

(56) References Cited

U.S. PATENT DOCUMENTS

| | | | |
|---|---|---|---|
| 4,787,882 A | 11/1988 | Claren | |
| 5,810,757 A | 9/1998 | Sweezer, Jr. et al. | |
| 6,461,327 B1 * | 10/2002 | Addis ................ | A61M 25/1011 |
| | | | 604/509 |

(Continued)

FOREIGN PATENT DOCUMENTS

| | | |
|---|---|---|
| EP | 0230040 A2 | 7/1987 |
| WO | 0134237 A1 | 5/2001 |
| WO | 2016022797 A1 | 2/2016 |

*Primary Examiner* — Rebecca E Eisenberg
*Assistant Examiner* — Kate Elizabeth Strachan
(74) *Attorney, Agent, or Firm* — Maschoff Brennan; Paul G. Johnson

(57) ABSTRACT

A venous drainage cannula, catheter, or other device is in certain embodiments convertible or adjustable for application in cardiac surgery procedures involving cardiopulmonary bypass. Such a convertible cannula device can be modified, for example, for use as both a multi-stage cannula and a bi-caval cannula, so that the same device can be used in multiple different procedures where one or the other cannula type is needed. Such convertible cannula or other device can simplify and reduce a number of parts needed for a bypass procedure, by providing one adjustable and versatile device to serve multiple functions where different cannulae are traditionally required. Various embodiments further provide cannula devices where a variety of different hole or opening arrangements and configurations can be achieved, to adapt to various different procedures.

20 Claims, 8 Drawing Sheets

(56) References Cited

U.S. PATENT DOCUMENTS

| | | | |
|---|---|---|---|
| 6,508,777 B1 * | 1/2003 | Macoviak | A61M 25/1011 |
| | | | 604/9 |
| 9,192,755 B2 | 11/2015 | Ravenscroft | |
| 2001/0000528 A1 | 4/2001 | Cho | |
| 2003/0004452 A1 * | 1/2003 | Lenker | A61M 1/3653 |
| | | | 604/4.01 |
| 2011/0160517 A1 * | 6/2011 | Smith | A61M 1/3666 |
| | | | 600/16 |
| 2015/0104331 A1 | 4/2015 | Dye | |
| 2015/0297810 A1 * | 10/2015 | Rubin | A61M 1/89 |
| | | | 604/542 |

* cited by examiner

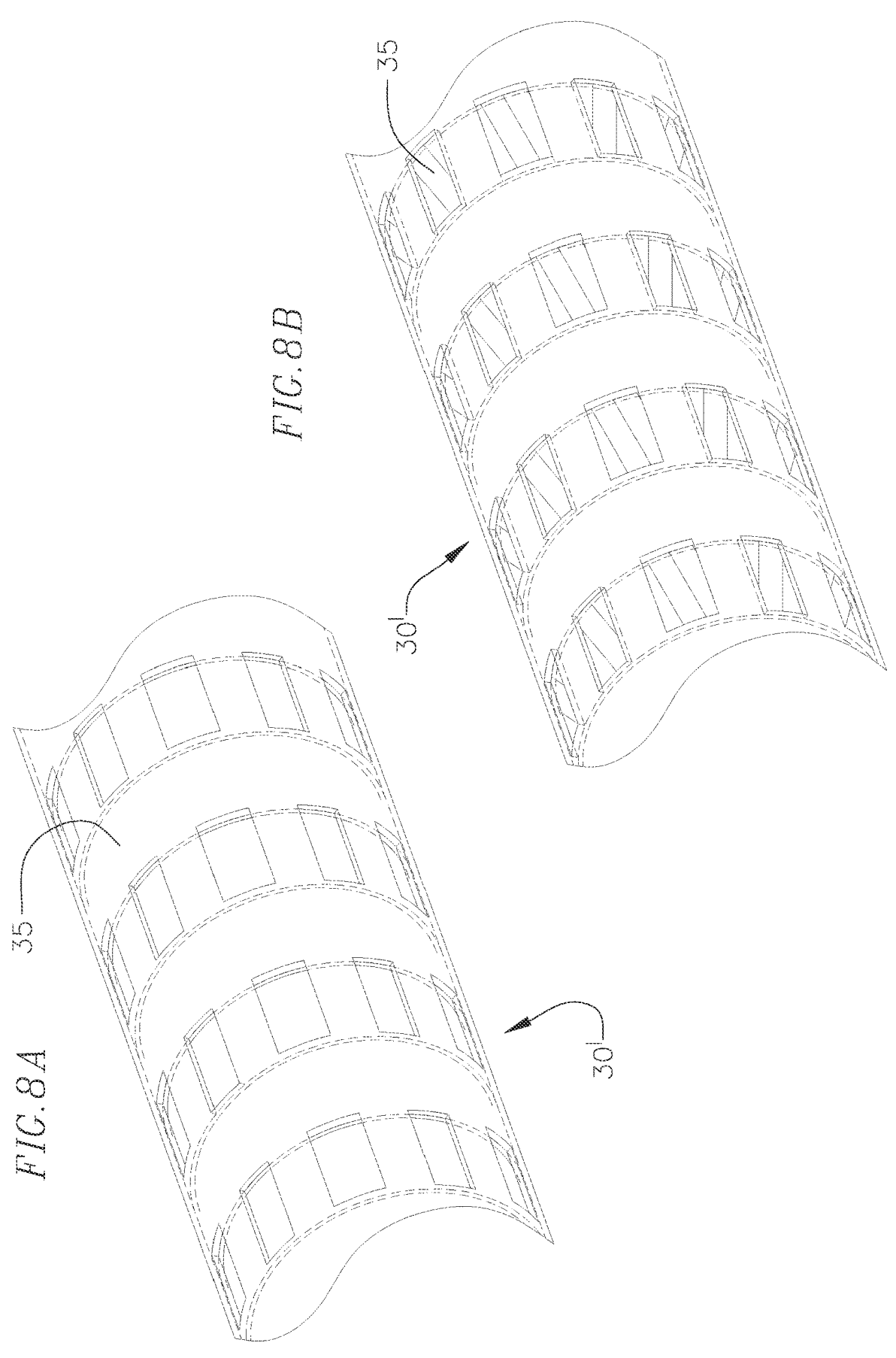

METHOD OF CONVERTING A FEMORAL VENOUS CANNULA

CROSS REFERENCE TO RELATED APPLICATIONS

This application is a continuation of U.S. application Ser. No. 16/513,575, filed Jul. 16, 2019, which is a continuation of International Patent Application No. PCT/US2017/013645, filed Jan. 16, 2017, the entire disclosures all of which are incorporated by reference.

BACKGROUND

Field

The present application generally concerns venous cannulae, and more specifically, to a venous drainage cannula or catheter that can be adjustable for application in various different cardiac surgery procedures involving cardiopulmonary bypass.

Description of Related Art

Various different surgical procedures are or can be performed using cardiopulmonary bypass. Such "on-pump" cardiopulmonary bypass procedures may be necessary or favorable in situations where heart function must be interrupted, while circulation must be continued in a patient. For example, in cardiac surgeries where the heart wall is opened to gain access to one or more chambers of the heart, cardiopulmonary bypass can be used to temporarily replace the heart function and support blood oxygenation and circulation, while the heart can be emptied of blood in order to more easily facilitate the particular surgical procedure.

During a cardiopulmonary bypass, a pump or similar machine is connected to the veins and arteries near the heart. Deoxygenated or venous blood that is returning to the heart is removed from the body by one or more cannulae or other devices. Generally, such cannulae are positioned in the right atrium, in the superior vena cava and/or the inferior vena cava, and/or further away from the heart, for example, in the femoral vein, to intercept the deoxygenated blood that would otherwise return to the heart. Withdrawn blood is then oxygenated and further processed, and returned to the body, for example, into the ascending aorta. In this manner, a patient's body can remain oxygenated while, for example, a cardiac procedure is being performed.

Traditionally, cardiopulmonary bypass surgery involves insertion of two separate venous cannula for separate blood withdrawal at the superior vena cava and the inferior vena cava. To prevent blood from entering the heart during a cardiac surgical procedure, a first cannula is positioned in the superior vena cava, and a second cannula is positioned in the inferior vena cava. In some instances, both the superior and inferior venae cavae are then clamped or otherwise sealed from the right atrium. In this manner, blood is drained or withdrawn from the body by the two cannulae prior to reaching the heart.

Recently, more research and emphasis has been placed on less invasive surgical procedures which involve, for example, a lower number of and/or smaller incisions for performing the same procedures. In the field of cardiac surgery, such procedural modifications may include reducing wound opening sizes and/or reducing the number of parts required at the surgical site. For example, mini-sternotomy approaches to heart valve repair or replacement procedures, where only part of the sternum or breastbone is split or separated to gain access to the heart, are gaining popularity in lieu of, for example, the same procedures where a standard sternotomy (i.e., where the entire sternum is separated) is performed.

Since a mini-sternotomy may only yield an incision that may be approximately half the length of an incision made in a standard sternotomy, there is a need or desire to reduce the number of surgical parts and instruments which require access to the main incision site. In recent years, femoral venous cannula have gained popularity in such procedures. Femoral venous cannulae are inserted through the femoral vein at or near the groin or thigh area, away from the surgical field. The cannula is advanced through the femoral vein and up through the inferior vena cava towards the heart. The end region of a femoral venous cannula is generally long, with multiple stages of openings, and is positioned to traverse the right atrium, with at least one set of openings positioned in the superior vena cava and one set of openings positioned in the inferior vena cava to effect blood drainage. Such a femoral venous cannula can therefore replace the use of the two separate single stage cannula used in traditional cardiopulmonary bypass procedures, and so reduces the total number of parts required for a cardiopulmonary bypass, and may also reduce the number of incisions that are required at the surgical site. Furthermore, since the access site of the femoral venous cannula is away from the surgical site (e.g., at the groin or thigh), the use of femoral venous cannulae can also serve to reduce clutter or crowding at the surgical site.

Generally, different femoral venous cannulae are used for procedures on the left and right sides of a heart, respectively. For example, for aortic valve or mitral valve replacement or repair, a multi-stage femoral venous cannula may be utilized, where drainage is performed on each of the superior vena cava, the inferior vena cava, and the right atrium. The use of a multi-stage cannula for these procedures may be beneficial, for example, for more effective blood drainage. Such multi-stage cannulae may include drainage openings along an entire end portion of the cannulae, for example, as seen in FIG. 1, so that the openings can be simultaneously positioned in the superior vena cava, the right atrium, and the inferior vena cava.

However, for some procedures, surgical access to the right atrium, or more generally to the right chambers of the heart, may be required, for example, for tricuspid valve replacement or repair. In these situations, a bi-caval drainage approach may be more desirable, where drainage occurs only at the superior vena cava and the inferior vena cava, but not at the right atrium, so that the surgical procedure can be more easily performed there. Typically, a different bi-caval cannula may be used in these circumstances, where openings at the end portion of the cannula are interrupted by a central or middle portion that does not include any openings, for example, as seen in FIG. 2. Use of such a bi-caval cannula can still drain blood at the superior and inferior venae cavae, while the right atrium is isolated for the surgical procedure.

SUMMARY

In some instances, multiple surgical procedures need to be made on a single patient. For example, a patient may require replacement or repair of an aortic or mitral valve, as well as a separate procedure on a tricuspid valve. Or more generally, a surgeon may need to perform separate procedures on the right and left sides of the heart of a patient. Previously, such situations involved the complete removal of a first type of femoral venous cannula after completion of the first procedure, and insertion of a second type of femoral venous cannula before beginning the second procedure.

An object of the invention is to provide a femoral venous cannula device that is adjustable between a multi-stage cannula and a bi-caval cannula, for example, to reduce the number of parts needed for cardiopulmonary bypass surgery. Another object of the invention is to provide such an adjustable cannula, to add flexibility and simplify procedures in situations where different cannulae are traditionally required. In accordance with the objects of the invention, embodiments of the invention provide a convertible femoral venous cannula that can be modified to be used in both procedures requiring a multi-stage cannula and procedures requiring a bi-caval cannula. Embodiments of the invention further provide a femoral venous cannula where a variety of different hole or opening configurations can be achieved, to adapt to various different procedures.

According to one embodiment, a device for use in cardiopulmonary bypass includes a cannula configured to be positioned in at least one of a right atrium, a superior vena cava, or an inferior vena cava of a patient, the cannula having a first end, a second end, and a longitudinal axis extending between the first end and the second end. The cannula includes a first section at the first end, the first section including an outer wall and having at least one opening therethrough, a second section connected to the first section along the longitudinal axis, the second section including an outer wall and having at least one opening therethrough, and a third section connected to the second section along the longitudinal axis on a side of the second section opposite the first section, the third section including an outer wall and having at least one opening therethrough. In a first configuration, the openings in each of the first section, the second section, and the third section are respectively open to inner spaces defined by the first section, the second section, and the third section. In a second configuration, the at least one opening in the second section is occluded to restrict communication with the inner space defined by the second section, while the openings in the first section and the third section remain open to the inner spaces defined by the first section and the third section, respectively.

According to another embodiment, a method is provided for adjusting and positioning a femoral venous cannula in a patient for cardiopulmonary bypass during a cardiac procedure. The cannula has a first end, a second end, and a longitudinal axis extending between the first end and the second end, and includes a first section at the first end and including an outer wall and having at least one opening therethrough, a second section connected to the first section along the longitudinal axis and including an outer wall and having at least one opening therethrough, and a third section connected to the second section along the longitudinal axis on a side of the second section opposite the first section and including an outer wall and having at least one opening therethrough. In a first configuration, the openings in each of the first section, the second section, and the third section are respectively open to inner spaces defined by the first section, the second section, and the third section, while in a second configuration, the at least one opening in the second section is occluded to restrict communication with the inner space defined by the second section, while the openings in the first section and the third section remain open to the inner spaces defined by the first section and the third section, respectively. The method includes adjusting the cannula to one of the first configuration or the second configuration, inserting the cannula through the femoral vein of the patient and advancing the cannula towards the heart of the patient, and positioning the cannula at a first position in the patient wherein the at least one opening of the first section of the cannula is arranged in the superior vena cava, the at least one opening of the second section of the cannula is arranged in the right atrium, and the at least one opening of the third section of the cannula is arranged in the inferior vena cava.

Embodiments of the invention therefore provide a femoral venous cannula device that is convertible between a multi-stage cannula and a bi-caval cannula for different surgical procedures.

BRIEF DESCRIPTION OF THE DRAWINGS

The foregoing and other features and advantages of the invention will become apparent from the following detailed description of embodiments, by means of the accompanying drawings. In the drawings:

FIGS. 6A and 6B show cross-sectional views of the femoral venous cannula of FIG. 4 in a first position and a second position, respectively, the cross-section taken in a plane perpendicular to the longitudinal axis of the cannula;

FIGS. 8A and 8B show an enlarged view of a femoral venous cannula according to a second embodiment of the invention, in a first position and a second position, respectively;

DETAILED DESCRIPTION

Figure 3:
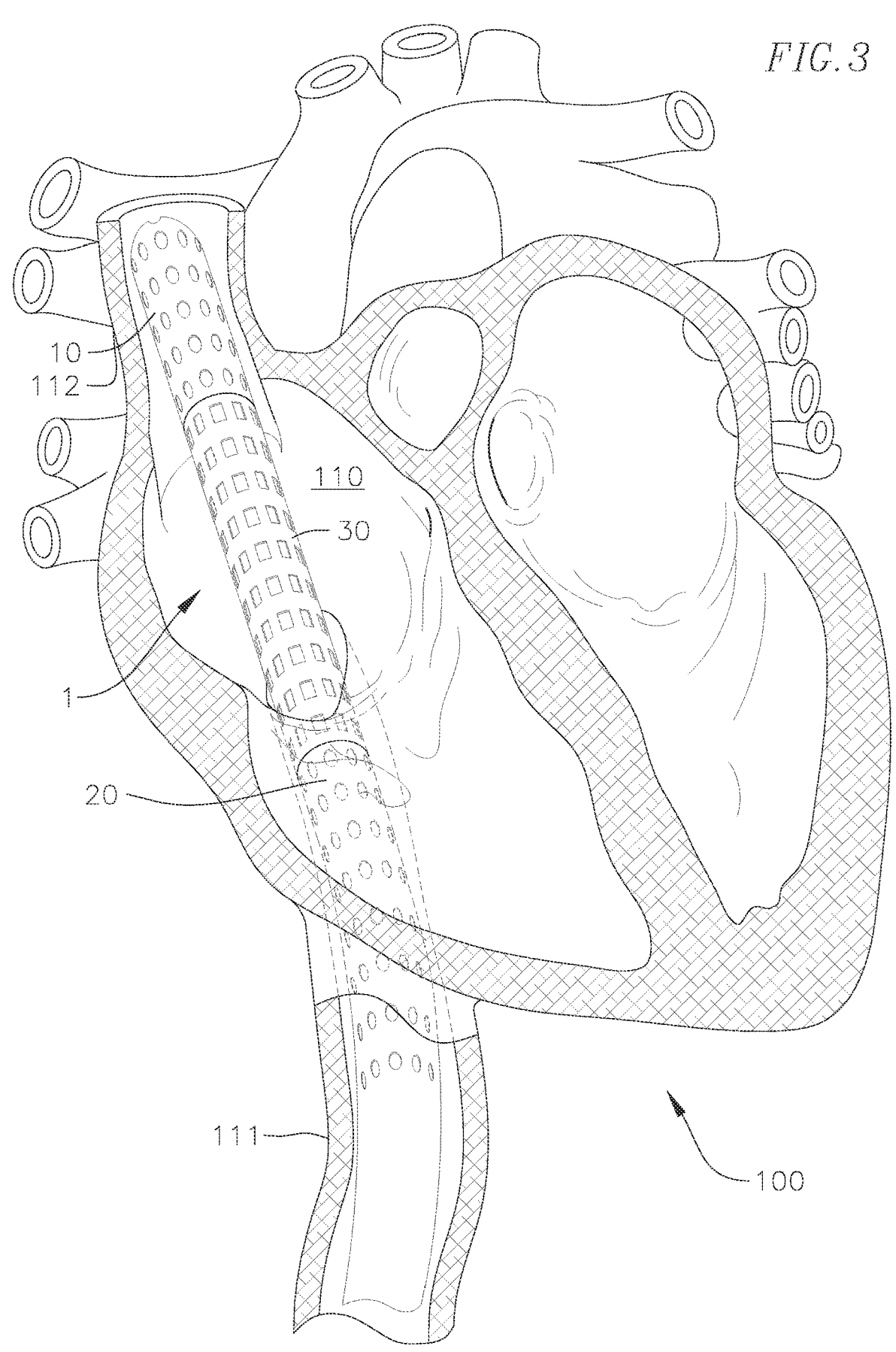
FIG. 3 shows a femoral venous cannula that is positioned at a heart for a cardiopulmonary bypass procedure according to an embodiment of the invention.

FIG. 3 shows a heart and a femoral venous cannula according to an embodiment of the invention. The right atrium 110 of the heart 100 is connected to the inferior vena cava 111, which connects the veins located in the lower part of the patient's body to the heart 100, and the superior vena cava 112, which connects the veins located in the upper part of the patient's body to the heart 100. Deoxygenated blood generally empties from the inferior vena cava 111 and the superior vena cava 112 into the right atrium 110, to be oxygenated and recirculated through the body.

In FIG. 3, a femoral venous cannula 1 according to an embodiment of the invention has been positioned through the inferior vena cava 111 and the right atrium 110, and protrudes into the superior vena cava 112. The cannula 1 is positioned in this manner to drain the patient's body of deoxygenated blood, and to deliver the blood to, for example, a cardiopulmonary bypass pump or machine, for oxygenation and further processing, before being returned to the patient's body.

Figure 4:
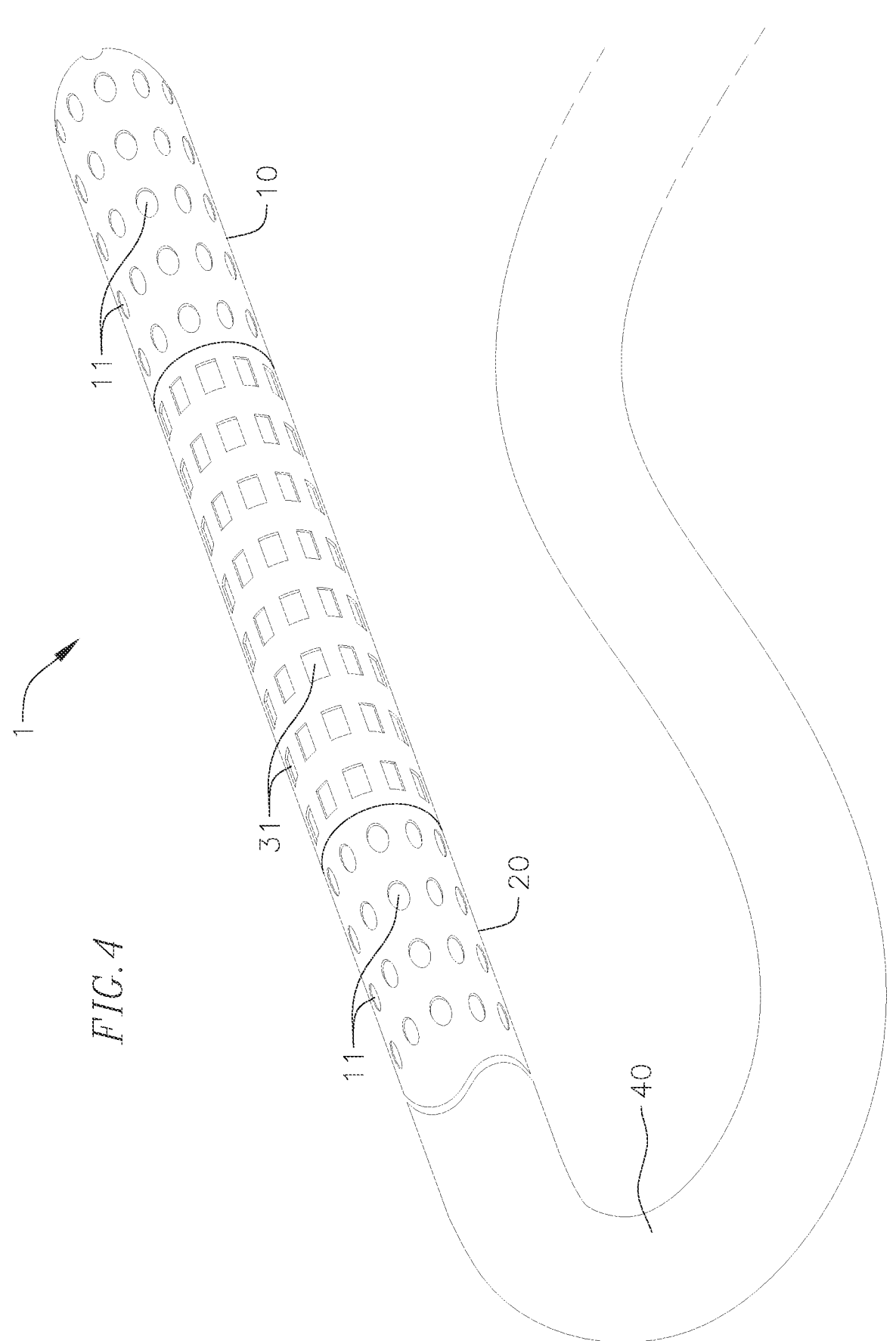
FIG. 4 shows a femoral venous cannula configured as a multi-stage cannula according to a first embodiment of the invention.

As can be seen in FIGS. 3 and 4, the cannula 1 according to an embodiment of the invention has a first section 10 and a second section 20. Each of the first and second sections 10, 20 may be substantially cylindrical. The sections 10, 20 are flexible to ease insertion and positioning in the body, and one or both sections 10, 20 may be wire reinforced. Each section 10, 20 includes at least one opening 11, and typically a plurality of openings 11. The openings 11 in FIGS. 3 and 4 are circular. The openings 11 in the first section 10 may be shaped and/or arranged substantially similarly to the openings 11 in the second section 20. In some embodiments, the openings 11 in the first section 10 may have different shapes and/or spacing than the openings 11 in the second section 20, based on the particular clinical application and/or patient characteristics. A distal end of the first section 10 of the cannula 1 may be tapered or otherwise shaped to further ease insertion of the cannula 1 through the body.

In the embodiment of FIGS. 3 and 4, the sections 10 and 20 are separated by a third section 30, which include one or more openings 31, and generally a plurality of openings 31. The openings 31 in the embodiment in FIGS. 3 and 4 are illustrated as being square or rectangular shaped to be more easily distinguishable from the openings 11. However, in other embodiments, the openings 31 may be the same shape (e.g., round, similar to how openings 11 are illustrated in the figures), and have the same spacing, as the openings 11 in either sections 10 or 20. The section 30 may be configured similarly to the sections 10 and 20. That is, the section 30 may also be substantially cylindrical, may be flexible, and/or may be wire-reinforced. In other embodiments, the section 30 may be configured differently than the sections 10 and 20, for example, the section 30 may be made of a semi-rigid material that is more rigid than a material used for the sections 10 and 20, and may not be wire-reinforced.

The sections 10, 20, 30 may further be connected to an elongated tubular section 40 that connects the cannula 1 to the outside of the patient, for example, first for facilitating insertion and positioning of the cannula 1, and later for connection to a cardiopulmonary bypass pump.

As can best be seen in FIG. 3, in a final position, the cannula 1 according to the first embodiment is positioned so that the first section 10 is located in or approximate the superior vena cava 112, the second section 20 is located in or approximate the inferior vena cava 111, and the central third section 30 is located in or approximate the right atrium 110 of the heart 100. Generally, a length of the central section 30 is sufficiently long to extend from the inferior vena cava 111 to the superior vena cava 112, so that the holes 11 in sections 10 and 20 are only positioned in the inferior and superior venae cavae 111, 112, and not in the right atrium 110. In some instances, different sized cannula with, for example, different widths or central sections 30 having different lengths, may be available for selection, depending on characteristics of the patient. The cannula 1 can be inserted, for example, via the femoral vein near the thigh or groin of the patient, and advanced towards the heart 100 through the inferior vena cava 111. In other embodiments, it may be possible to insert the cannula 1 in the opposite direction via the superior vena cava 112, or from another access point. In FIG. 3, the cannula 1 is configured as a multi-stage cannula, where the holes or openings 11 and 31 in each of the sections 10, 20, and 30 are open and facilitate drainage of deoxygenated blood from the body. The multi-stage cannula configuration illustrated in FIGS. 3 and 4 may be used, for example, during aortic or mitral valve replacement or repair procedures.

Meanwhile, embodiments of the invention provide a convertible cannula, where the central section 30 of the cannula 1 can be adjusted so that the openings 31 are sealed shut instead of kept open, to effectively convert the cannula 1 from a multi-stage cannula to a bi-caval cannula, so that the same cannula 1 can be used for different cardiac surgeries and procedures which require either type of cannulation.

In the embodiment of FIGS. 3 and 4, section 30 of cannula 1 includes a shutter system. Referring to the cross-sections in FIGS. 5, 6A, and 6B (where FIGS. 6A and 6B shows cross-sections of section 30 of cannula 1 in different positions or configurations, described in greater detail below), at the section 30, the cannula 1 may include an outer wall 32 and an inner wall 34, where the inner wall 34 defines an inner lumen 12, and where a separate space is formed between the inner wall 34 and the outer wall 32. The inner lumen 12 may connect to the section 10 at the distal end of the cannula 1, for example, for facilitating drainage from the openings 11 in section 10. The outer wall 32 defines the openings 31, which extend through the outer wall 32 into a space between the inner wall 34 and the outer wall 32, to facilitate drainage by the cannula 1 through the openings 31. In some embodiments, the inner lumen 12 may also communicate with the space between the inner wall 34 and the outer wall 32, or the inner wall 34 may be omitted, so that the openings 11 and 31 open into a same space inside the cannula 1. The shutter system further includes at least one sliding wall 33 positioned along an inner surface of the outer wall 32. The sliding wall 33 may include a plurality of longitudinal strips that extend along a length of the section 30 between the sections 10 and 20. Alternatively, the sliding wall 33 may be a substantially cylindrical wall that is slightly smaller in diameter or width than the outer wall 32, and that includes openings that are either substantially the same size or larger than the openings 31.

Figure 5:
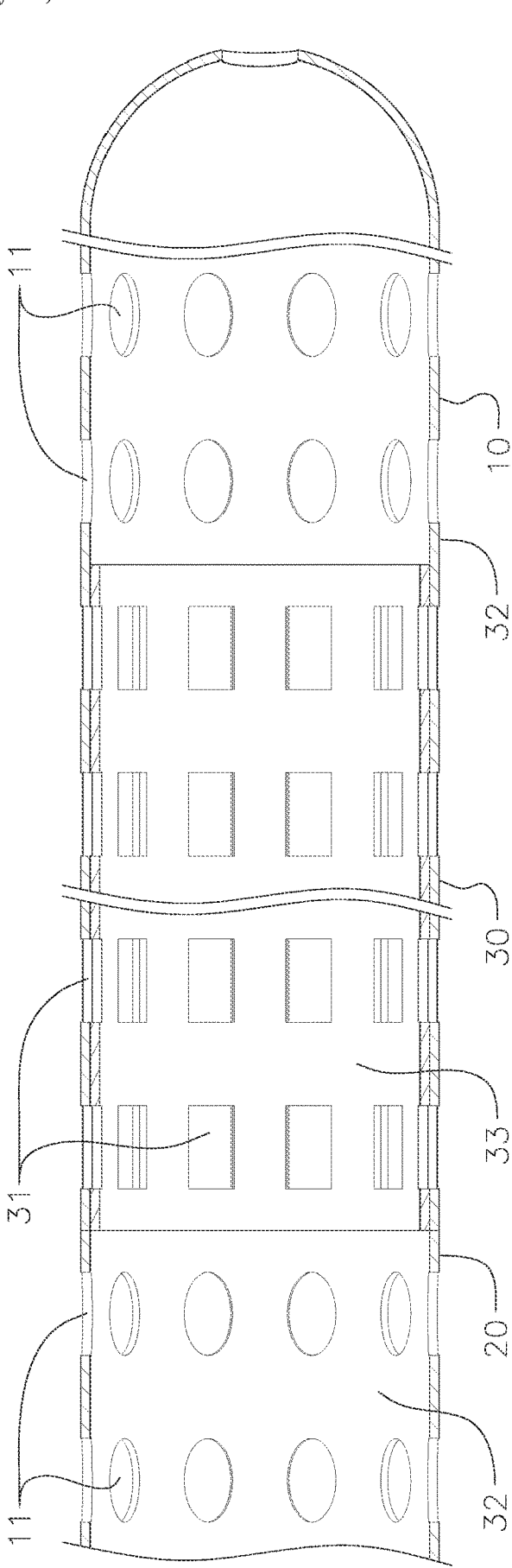
FIG. 5 shows a cross-sectional view of the femoral venous cannula of FIG. 4, where the cross section includes a longitudinal axis of the cannula.
Figures 6A, 6B:
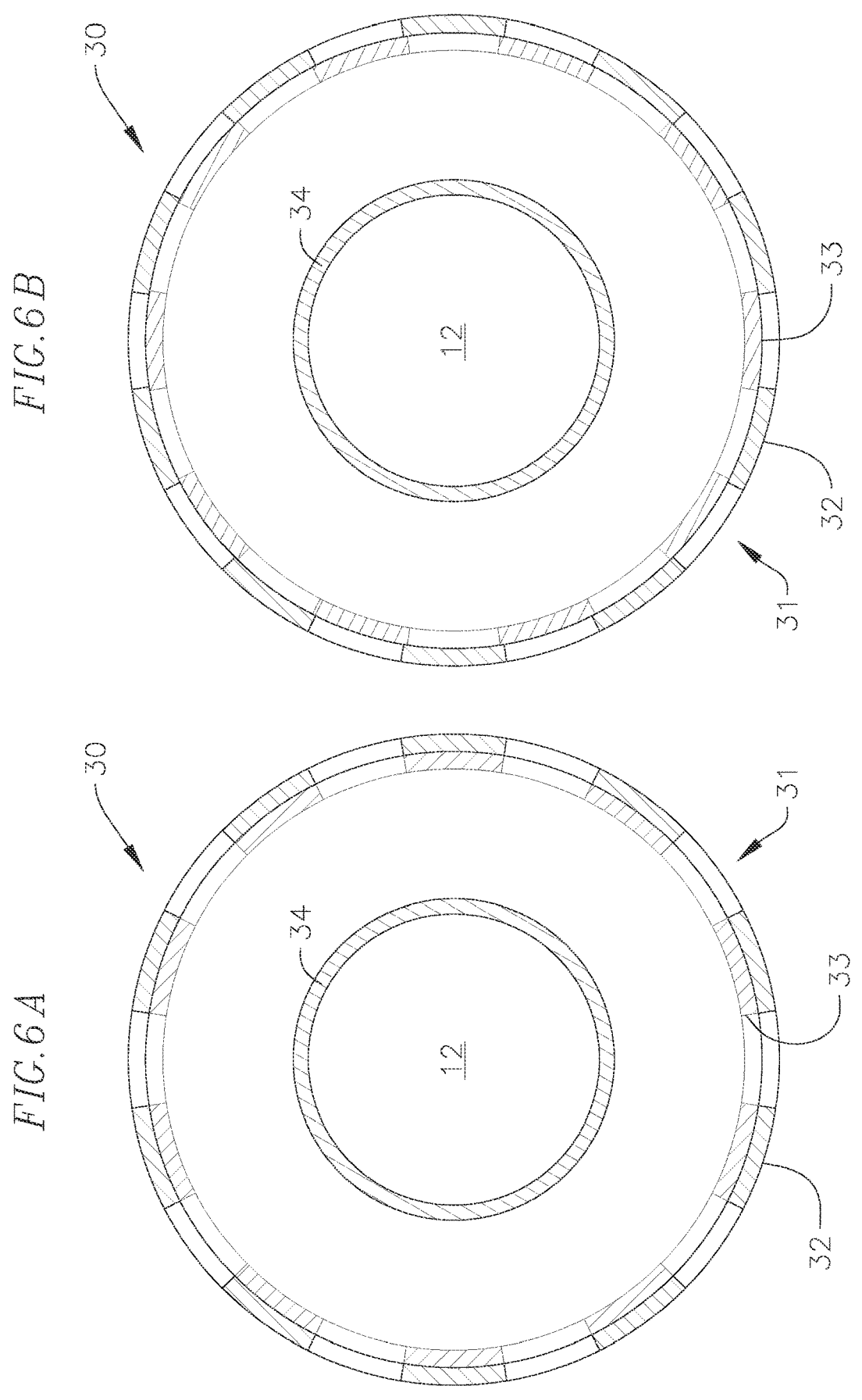
Figure 7:
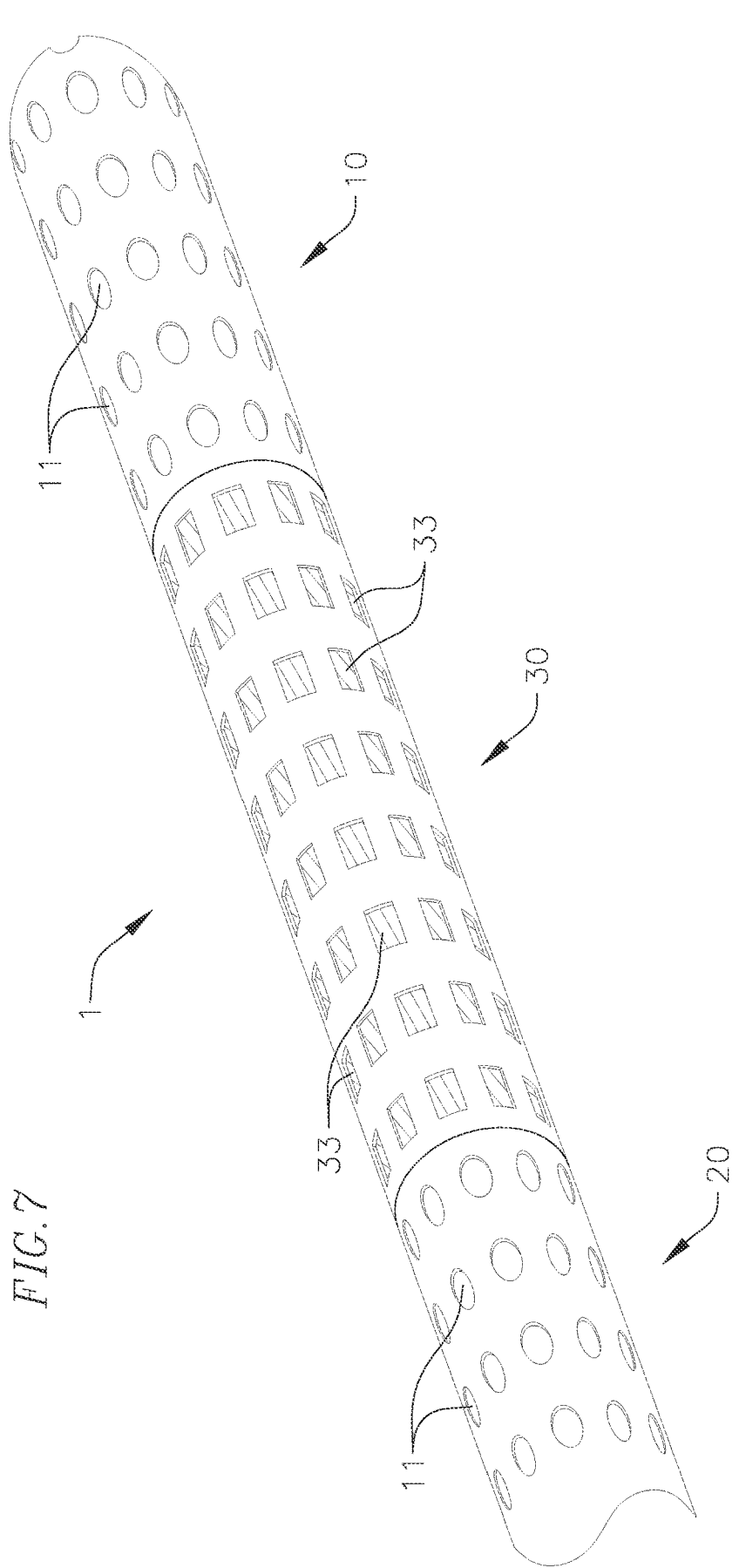
FIG. 7 shows an enlarged view of an end the femoral venous cannula of FIG. 4, where the cannula is configured as a bi-caval cannula.

In a first position, as illustrated in FIGS. 5 and 6A, the sliding wall 33 is positioned so that the openings in the sliding wall 33 are aligned with the openings 31 in the outer wall 32, so that the sliding wall 33 does not block the openings 31 or obstruct access into the space between the inner wall 34 and the outer wall 32. In a second position, as illustrated in FIGS. 6B and 7, the sliding wall 33 can be rotated relative to the outer wall 32 of section 30 so that the sliding wall 33 occludes or blocks the openings 31, and thus blocks access into the cannula 1 from the openings 31, while the openings 11 of cannula 1 remain open. Therefore, in the configuration shown in FIG. 7, the cannula 1 has been converted to function as a bi-caval cannula, where drainage occurs at the inferior and superior venae cavae 111, 112 through sections 20, 10, but no longer occurs at the right atrium 110, since the openings 31 are now blocked. The bi-caval cannula configuration illustrated in FIG. 7 may be used, for example, during procedures where access to the right chambers of the heart are required, such as during tricuspid repair or replacement, and/or where drainage at the right atrium 110 may not be needed or desired, or may hinder or obstruct the particular procedure.

In the manner described above, the internal sliding wall 33 slides over the holes 31 in section 30, effectively opening and closing the holes 31 based on the requirements of the particular procedure. In one embodiment, the shutter system in FIGS. 3-7 may be remotely activated, for example, through an electronic switch system that can be actuated from outside the patient's body. In another embodiment, the sliding wall 33 may be mechanically rotated, for example, via a lever or similar mechanism at or near the section 30 of the cannula, or for example, a similar mechanism that connects to the outside of the patient's body through the tubular section 40.

In a second embodiment, illustrated in FIGS. 8A and 8B, a central section 30' of a cannula may instead include one or more sliding walls 35 that move laterally or longitudinally along the length of the cannula, rather than rotate relative to the rest of the cannula. The sliding wall 35 in FIGS. 8A and 8B may include, for example, a series of ring-shaped strips that are slightly smaller in diameter or width than the outer wall 32, or may include one substantially cylindrical wall that has openings substantially the same size or larger than the openings 31. As discussed above, actuation of the sliding wall 35 moves the wall 35 longitudinally, either towards the section 10 or towards the section 20, so that the sliding wall 35 occludes the openings 31, as can be best seen in FIG. 8B. The other portions of the cannula in FIGS. 8A and 8B may be similar to those discussed with respect to FIGS. 3-7.

Various modifications can also be made to the embodiments of the femoral venous cannula 1 in FIGS. 3-7 and in FIGS. 8A-8B. For example, in the embodiments discussed above, the sliding shutter walls 33, 35 are located along an inner surface of outer wall 32. However, in some embodiments, the sliding walls 33, 35 can be positioned on the outside of the cannula, or can be tightly sandwiched between two layers of the section 30. Furthermore, the sections 30, 30' and/or the sliding shutter wall 33, 35 are described as being semi-rigid and made of a stiffer material than a material of the sections 10 and 20, but in some embodiments, the sections 30, 30' and/or the sliding shutter wall 33, 35 may be constructed similarly to the sections 10, 20, and can also be wire-reinforced. Various other modifications can also be made to the described embodiments without departing from the general scope of the invention.

Figures 1, 2:
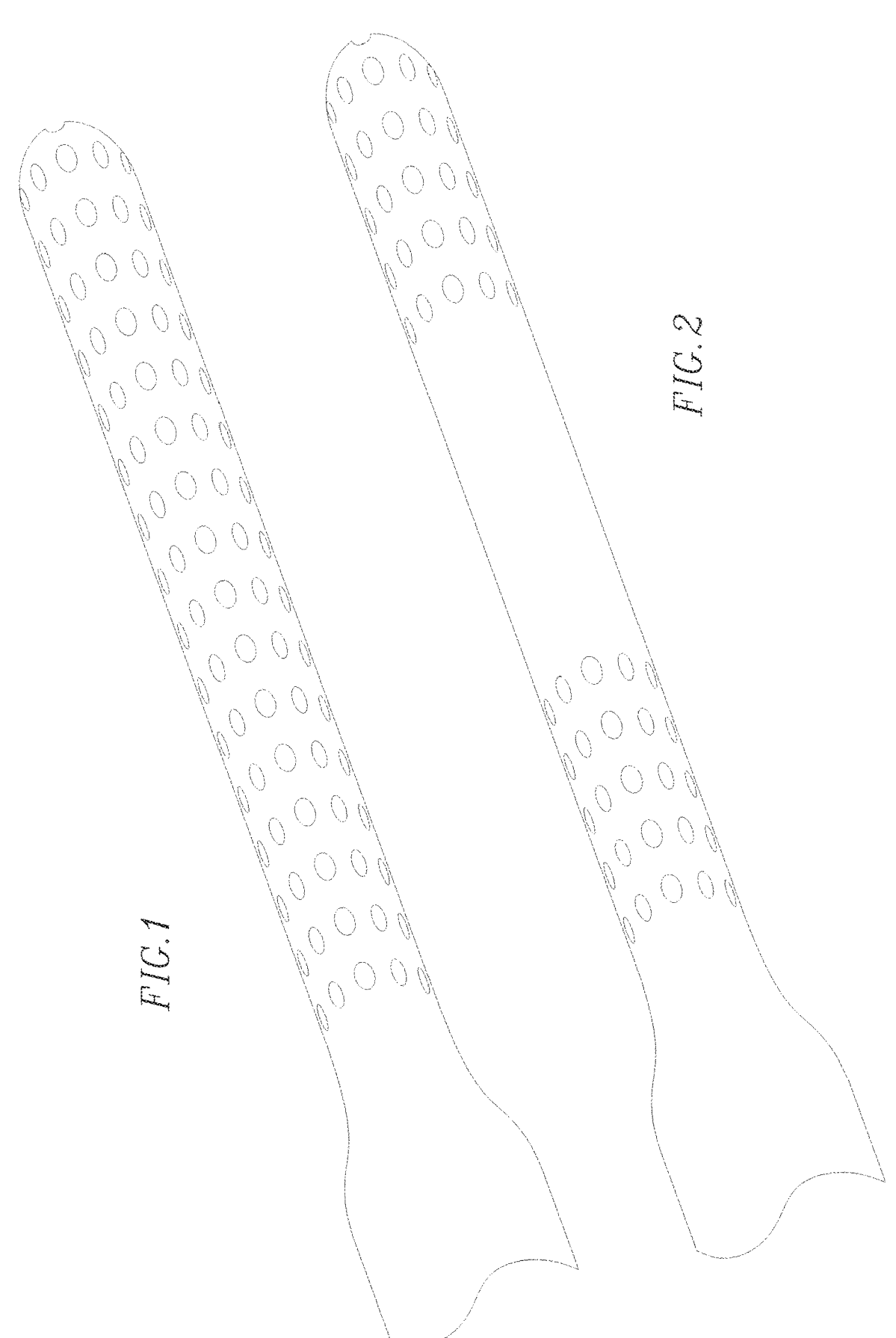
FIG. 1 shows a multi-stage femoral venous cannula.
FIG. 2 shows a bi-caval femoral venous cannula.
Figures 9A, 9B, 10:
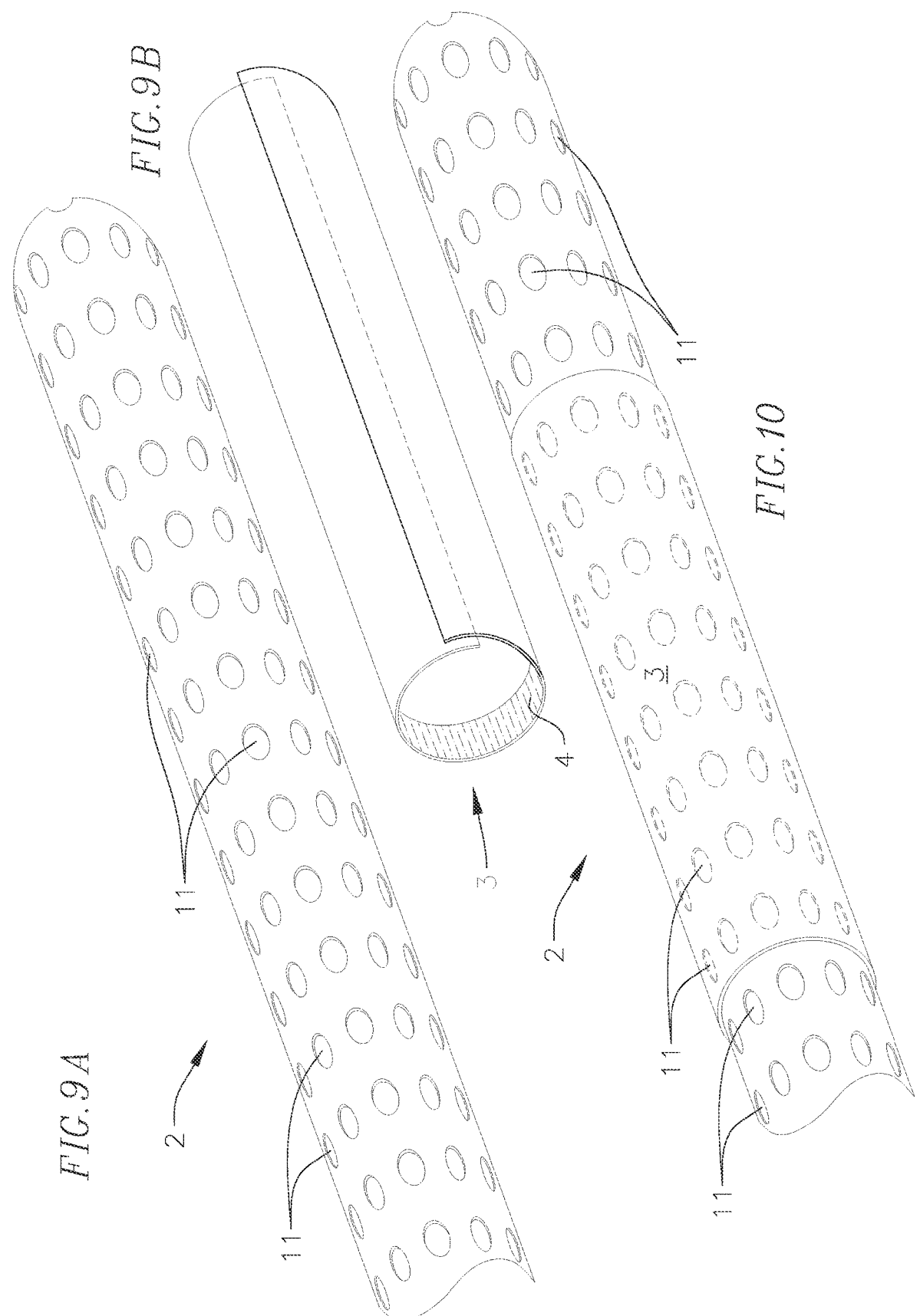
FIGS. 9A and 9B show a multi-stage femoral venous cannula and a sleeve, respectively, according to a third embodiment of the invention.
FIG. 10 shows the cannula and the sleeve in FIGS. 8A and 8B in an assembled state.

A third embodiment of the invention is illustrated in FIGS. 9A, 9B, and 10. In the third embodiment of the invention, a kit including a cannula 2 and an elastic tube or covering sheath 3 are provided. The cannula 2 can be, for example, a general multi-stage femoral venous cannula, such as the multi-stage cannula illustrated in FIG. 1. The cannula can include a plurality of holes or openings 11 along the length of the cannula 2, which are spaced apart and extend sufficiently along a length of the cannula 2 for the openings 11 to be positionable in the right atrium 110, the inferior vena cava 111, and the superior vena cava 112 of a patient simultaneously.

The elastic sheath or tube 3 is generally constructed of a material so as to be impermeable to blood. Furthermore, the tube 3 may include, for example, an adhesive 4 that is applied along the ends of the tube 3 (as illustrated), or alternatively, along an entire inner surface of the tube 3. The adhesive 4 provided will generally be strong enough to allow the tube 3 to permanently adhere to the cannula 2. The adhesive may initially be rolled out or covered, and then uncovered or rolled down once the tube 3 is arranged at a desired position relative to the cannula 2. Other variants of the adhesive type and/or application with respect to the surfaces of the tube 3 can also be used. For example, the tube 3 can adhere to the cannula through adhesives as discussed, or for example, via elastic properties or an interference fit. In some embodiments, a shrink wrap or similar material may be utilized for covering the desired openings 11 in cannula 2.

In operation, for example, after a procedure where a multi-stage cannula is utilized has been completed, a surgeon or other practitioner can attach the tube 3 over the cannula 2 through, for example, a puncture or access site through the heart wall, or alternatively, tube 3 can be attached upon removal of the cannula 2 from the patient's body. The adhesive or other adhering means will hold the tube 3 in position on the cannula 2, generally to cover the central openings 11 corresponding to the position of the right atrium, so that the modified cannula 2 can function as a bi-caval cannula during a subsequent procedure.

In the embodiment of FIGS. 9A-10, the elastic sheath or tube 3 can be applied to currently existing multi-stage femoral venous cannula, and so additional cannulae according to the invention may not need to be provided. By covering the openings 11 along a central portion of the cannula 2, the cannula 2 can be converted from a multi-stage cannula to a bi-caval cannula, so long as openings 11 remain uncovered at both a distal end and a proximal end relative to the positioning of the tube 3. The kit including cannula 2 and tube 3 may also be advantageous in that tubing of different sizes, lengths, and/or configurations can be provided, to provide a simple customizable cannula based on the particular patient's anatomy.

The parts of the cannulae 1, 2 according to embodiments of the invention are preferably made from one or more biocompatible materials, and may all be made of the same material, or can be made of different materials.

Each of the embodiments discussed above provides a single cannula that can be converted from a multi-stage cannula to a bi-caval cannula on demand, where a physician or other practitioner can close different holes along the cannula to adjust the hole configurations of the cannula to suit the particular clinical application. In some embodiments, the cannula can further be converted from a bi-caval cannula to a multi-stage cannula as well, for example, by opening different holes, adding more flexibility for the physician.

Embodiments of the invention would provide a cannula that would allow for customization of hole configurations, which could potentially reduce the number of products or product codes to stock. For example, cannulae according to embodiments of the invention could replace both multi-stage cannula and bi-caval cannula, so that only a single type of cannulae can be stocked to cover both types of applications. Embodiments of the invention would also allow more flexibility with respect to customization based on surgeon preference and patient anatomy, for example, different heart and/or vein sizes.

In addition, embodiments of the invention provide a more flexible cannula that can be adjusted mid-procedure. Previously, in instances where one of a multi-stage cannula or a bi-caval cannula is required for a first procedure, and then the other of the multi-stage cannula or the bi-caval cannula is required for a second procedure, upon completion of the first procedure, the first cannula had to be removed and the second cannula then inserted and repositioned before the second procedure could be performed. With embodiments of the invention, a single cannula can be positioned for the first procedure, and for example, adjusted to first serve as a multi-stage cannula, and can then be converted for the second procedure, for example, to serve as a bi-caval cannula, while still correctly positioned relative to the heart, so that removal and repositioning of the cannula is no longer required, thereby reducing surgical times and simplifying the surgical process. In addition, for example, with the third embodiment discussed above, a conventional multi-stage cannula can still be used for a first procedure, and tubing of different lengths can be provided, where an appropriate sealing tube can potentially be selected or cut mid-procedure, and then applied to the cannula, to seal the desired number of openings on the cannula based on the patient's anatomy, thereby providing a more customizable and effective bi-caval cannula.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples of the invention and should not be taken as limiting the scope of the disclosure. Rather, the scope of disclosure is defined by the following claims.

What is claimed is:

1. A method of heart surgery on a patient, the method comprising:

readying a cannula for insertion in the patient's vasculature, the cannula having a distal end, a proximal end, and a longitudinal axis extending between the distal end and the proximal end, and the cannula having a length sufficient to extend from outside the body to at least the superior vena cava and having:

a distal section at the distal end, the distal section comprising an outer wall and having a plurality of spaced openings in the outer wall distributed circumferentially and longitudinally therearound and open to an inner space within the cannula;

a central section in series with the distal section along the longitudinal axis, the central section comprising an outer wall and having a plurality of spaced openings in the outer wall distributed circumferentially and longitudinally therearound and open to the inner space within the cannula; and a proximal section in series with the central section along the longitudinal axis on a side of the central section opposite the distal section, the proximal section comprising an outer wall and having a plurality of spaced openings in the outer wall distributed circumferentially and longitudinally therearound and open to the inner space within the cannula;

inserting the distal end of the cannula into the femoral vein at or near the groin or thigh area;

advancing the cannula through the femoral vein and up through the inferior vena cava towards the heart until a conversion position is reached wherein the distal section is located in the superior vena cava, the central section is located in the right atrium, and the proximal section is located in the inferior vena cava, wherein the central section is sufficiently long to extend from the inferior vena cava to the superior vena cava, so that the openings in distal and proximal sections are only positioned in the inferior and superior venae cava, and not in the right atrium;

establishing the patient on cardiopulmonary bypass, including suctioning blood inward through the openings in the distal section, central section, and proximal section into the inner space within the cannula, and drawing the blood longitudinally through the cannula inner space to a cardiopulmonary bypass machine;

performing a procedure within the left atrium and/or the left ventricle;

while the cannula is in the conversion position, converting the cannula from a multi-stage cannula to a bi-caval cannula by closing the openings in the central section without changing the cannula location, and performing a procedure within the right atrium and/or the right ventricle while continuing to draw the blood longitudinally through the cannula to the cardiopulmonary bypass machine.

2. The method of claim 1, wherein the cannula includes a shutter wall member slidingly disposed along the central section, the shutter wall member having a plurality of apertures in between solid wall portions, wherein the apertures of the shutter wall member are aligned with the openings in the central section to enable the cannula to function as a multi-stage cannula, and the solid wall portions are aligned with and occlude the openings in the central section to enable the cannula to function as a bi-caval cannula.

3. The method of claim 2, wherein in a first position of the shutter wall member relative to the cannula configuration, the apertures are aligned with the openings in the central section, and in a second position of the shutter wall member the wall portions are aligned with and occlude the openings in the central section, while the openings in the distal section and the proximal section remain open to the inner space.

4. The method of claim 3, wherein the wall portions are longitudinal strips, and the shutter wall member rotates circumferentially around the longitudinal axis to move between the first position and the second position.

5. The method of claim 3, wherein the wall portions are ring-shaped strips, and the shutter wall member moves longitudinally towards either the distal end or the proximal end of the cannula to move between the first position and the second position.

6. The method of claim 2, wherein the shutter wall member is configured to be more rigid than the distal, central and proximal sections of the cannula.

7. The method of claim 2, wherein the shutter wall member and the central section of the cannula are configured to be more rigid than the distal and proximal sections of the cannula.

8. The method of claim 2, wherein the shutter wall member is located within the outer wall of the central section.

9. The method of claim 2, wherein the openings in the distal and proximal sections are circular, and the openings in the central section are rectangular.

10. The method of claim 1, wherein the procedure within the right atrium and/or the right ventricle comprises a tricuspid valve replacement or repair.

11. A method of heart surgery on a patient, the method comprising:

readying a cannula for insertion in the patient's vasculature, the cannula having a distal end, a proximal end, and a longitudinal axis extending between the distal end and the proximal end, and the cannula having a length sufficient to extend from outside the body to at least the superior vena cava and having:

a distal section at the distal end, the distal section comprising an outer wall and having a plurality of spaced openings in the outer wall distributed circumferentially and longitudinally therearound and open to an inner space within the cannula;

a central section in series with the distal section along the longitudinal axis, the central section comprising an outer wall and having a plurality of spaced openings in the outer wall distributed circumferentially and longitudinally therearound and open to the inner space within the cannula;

a proximal section connected to the central section distally along the longitudinal axis on a side of the central section opposite the distal section, the proximal section comprising an outer wall and having a plurality of spaced openings in the outer wall distributed circumferentially and longitudinally therearound and open to the inner space within the cannula; and a shutter wall member slidingly disposed within the inner space, the shutter wall member having a plurality of apertures in between solid wall portions;

inserting the distal end of the cannula into the femoral vein at or near the groin or thigh area;

advancing the cannula through the femoral vein and up through the inferior vena cava towards the heart until a conversion position is reached wherein the distal section is located in the superior vena cava, the central section is located in the right atrium, and the proximal section is located in the inferior vena cava, wherein the central section is sufficiently long to extend from the inferior vena cava to the superior vena cava, so that the openings in distal and proximal sections are only positioned in the inferior and superior venae cava, and not in the right atrium;

establishing the patient on cardiopulmonary bypass, including suctioning blood inward through the openings in the distal section, central section, and proximal section into the inner space within the cannula, and drawing the blood longitudinally through the cannula inner space to a cardiopulmonary bypass machine;

performing a procedure within the left atrium and/or the left ventricle;

while the cannula is in the conversion position, converting the cannula from a multi-stage cannula to a bi-caval cannula by closing the openings in the central section without changing the cannula location, wherein in a first position of the shutter wall member the apertures are aligned with the openings in the central section to enable the cannula to function as a multi-stage cannula, and after moving the shutter wall member from the first position to a second position, the solid wall portions are aligned with and occlude the openings in the central section to enable the cannula to function as a bi-caval cannula, while the openings in the distal section and the proximal section remain open to the inner space, and performing a procedure within the right atrium and/or the right ventricle while continuing to draw the blood longitudinally through the cannula to the cardiopulmonary bypass machine.

12. The method of claim 11, wherein the wall portions are longitudinal strips, and the shutter wall member rotates circumferentially around the longitudinal axis to move between the first position and the second position.

13. The method of claim 11, wherein the wall portions are ring-shaped strips, and the shutter wall member moves longitudinally towards either the distal end or the proximal end of the cannula to move between the first position and the second position.

14. The method of claim 11, wherein the shutter wall member is configured to be more rigid than the distal, central and proximal sections of the cannula.

15. The method of claim 11, wherein the shutter wall member and the central section of the cannula are configured to be more rigid than the distal and proximal sections of the cannula.

16. The method of claim 11, wherein the openings in the distal and proximal sections are circular, and the openings in the central section are rectangular.

17. The method of claim 11, wherein the openings in the central section are rectangular.

18. The method of claim 17, wherein the wall portions are longitudinal strips, and the shutter wall member rotates circumferentially around the longitudinal axis to move between the first position and the second position.

19. The method of claim 17, wherein the wall portions are ring-shaped strips, and the shutter wall member moves longitudinally towards either the distal end or the proximal end of the cannula to move between the first position and the second position.

20. The method of claim 11, wherein the procedure within the right atrium and/or the right ventricle comprises a tricuspid valve replacement or repair.

* * * * *